United States Patent [19]

Edwards et al.

[11] Patent Number: 4,735,651

[45] Date of Patent: Apr. 5, 1988

[54] NOVEL PHYTOTOXIC AND PLANT GROWTH REGULATING OLIGOPEPTIDE

[75] Inventors: Judson V. Edwards; Alan R. Lax, both of New Orleans, La.

[73] Assignee: The United States of America as represented by the Secretary of Agriculture, Washington, D.C.

[21] Appl. No.: 886,502

[22] Filed: Jul. 17, 1986

[51] Int. Cl.$^4$ .................... A01N 37/36; A01N 37/10; A01N 37/18; C07K 5/08

[52] U.S. Cl. .................................... 71/108; 71/115; 71/118; 530/330; 530/331

[58] Field of Search ................. 530/330, 331; 71/108, 71/115, 118

[56] References Cited

PUBLICATIONS

Rich et al, Chem. Abstr., vol. 88, No. 62600w (1978).
Myer, W. L.; Kuyper, L. F., Lewis, R. B., Templeton, G. E. and Woodhead S. H., Biochem. Biophys. Res. Comm. 56:234–240 (1974).
Walton, J. D., Elizabeth D. Earle, and Bradford W. Gibson, Biochem. Biophys. Res. Comm. Toxin from *Helminthosporium carbonum* Race 1.107:785, (1982).
Rich, Daniel H., J. Tam, P. Mathiaparanam, J. Grant, Synthesis, "Selective N–Methylation of Dehydroamino Acids and Peptides", pp. 402–404.
Rich, Daniel H. and Fradip K. Bhatnagar, "Conformational Studies of Tentoxin by Nuclear Magnetic Resonance Spectroscopy, Evidence for a New Conformation for a Cyclic Tetrapeptide", *Journal of the American Chemical Society* 100:7:2212–2218 (1978).
Kato, Tetsuo, Akira Tone, Yasushi Kodera, Sannamu Lee, Yasuyuki Shimohigashi and Nobuo Izumiya, "Conformation of Cyclo(-L Pro–D–Leu–D–Tyr(-ME)–L–ILE–) Predicted by Empirical Rules for Cyclic Tetrapeptides was Evidenced by $^1$H– and $^{13}$C–NMR Spectroscopy", submitted *Chemistry Letters*.

*Primary Examiner*—John Kight
*Assistant Examiner*—Christina Chan
*Attorney, Agent, or Firm*—M. Howard Silverstein; David G. McConnell; Raymond C. Von Bodungen

[57] ABSTRACT

The following novel oligopeptide compounds which possess phytotoxic and plant growth regulating properties and methods for their use are disclosed: $R_1$-N($R_2$)-D,L-Ala-D,L-Leu-N($R_2$)ΔPhe-Gly-O$R_3$; in which $R_1$ is H or a protecting group at the amino terminus of the type 9-fluorenylmethoxycarbonyl, or benzyloxycarbonyl, $R_2$ is an alkyl of 2 to 3 carbon atoms, $R_3$ is hydrogen or an alkyl of 2 to 3 carbon atoms, and ΔPhe is dehydrophenylalanine. $R_1$-D,L-Leu-N($R_4$)-ΔPhe-Gly-O$R_3$; $R_1$Aib-N($R_2$)-ΔPhe-Gly-O$R_3$; $R_1$-Ala-N($R_5$)-ΔPhe-Gly-O$R_3$; $R_1$-Val-N($R_2$)-ΔPhe-Gly-O$R_3$; wherein $R_1$ is H or a protecting group at the amino terminus of the type tert-butyloxycarbonyl-(BOC), 9-fluorenylmethyloxycarbonyl, or benzyloxycarbonyl, $R_2$ is an alkyl of 1 to 3 carbon atoms, $R_3$ is hydrogen or an alkyl of 1 to 3 carbon atoms, and ΔPhe is dehydrophenylalanine.

23 Claims, No Drawings

NOVEL PHYTOTOXIC AND PLANT GROWTH REGULATING OLIGOPEPTIDE

BACKGROUND OF THE INVENTION (1) Field of the Invention

This invention relates to new oligopeptides compounds that demonstrate phytotoxic and plant growth regulating properties.

(2) Description of the Prior Art

The cyclic tetrapeptides HC toxin and tentoxin have been isolated from fungal culture filtrates, structurally characterized, and screened for their phytotoxic activities. Tentoxin which has the sequence cyclo [L-Leucyl-N-methyl-(Z)-dehydrophenylalanyl-glycyl-N-methyl-L-alnyl] was originally isolated from fungal culture filtrates of *Alternaria tenuis* and described as a non-host specific toxin [Meyer, W. L.; Kuyper, L. F., Lewis, R. B., Templeton, G. E. and Woodhead S. H., Biochem Biophys. Res. Comm. 56: 234–240 (1974)]. Biologically, tentoxin induces chlorosis in lettuce, potato, cucumber and spinach but not in radish, corn and some species of tobacco. This biological activity has been directly correlated with the conformation of the cyclic tetrapeptide, (Rich, D. H. and Bhatnagar, P. K., J. Am. Chem. Soc. 100:7, 2212–2218. Kato, T., Tone A., Kodera, Y., Lee, S., Shimohigashi, Y., and Izumiya, N., Chemistry Letters, pp. 1209–1212, 1985. HC toxin, which has the sequence cyclo [L-2-amino-9-10-epoxy-8-oxo-decanoyl)-D-prolyl-L-alanyl-alanyl] was originally isolated as a host-specific toxin from *Helminthosporium carbonum* [J. D. Walton, Elizabeth D. Earle, and Bradford W. Gibson, Biochem. Biophys. Res. Comm., 107: 785 , (1982)] and biologically characterized for its root growth inhibition of susceptible maize hybrids.

SUMMARY OF TTHE INVENTION

Previous work on naturally occurring peptides which demonstrated phytotoxic or plant growth regulating activity taught that cyclic ring closure was essential for biological activity. The compounds of the preferred embodiment of this invention clearly demonstrate that simple acyclic peptides (synthetically derived) contain key structural functionalities and are highly active as root growth inhibitors in germinating seedlings. This invention comprises novel oligopeptide compounds which possess phytotoxic and plant growth regulating properties of the following general formulas and methods for their use:

I. $R_1$-N($R_2$)-D,L -Ala-D,L-Leu-N($R_2$)$\Delta$Phe-Gly-O$R_3$;
II. R-D,L-Leu-N($R_2$)$\Delta$Phe-Gly-O$R_3$;
III. $R_1$-Aib-N($R_2$)$\Delta$Phe-Gly-O$R_3$;
IV. $R_1$-Ala-N($R_5$)$\Delta$Phe-Gly-O$R_3$;
V. $R_1$-Val-N($R_2$)$\Delta$Phe-Gly-O$R_3$;

for Formula I, $R_1$ is H or a protecting group at the amino terminus of the type 9-fluorenylmethyloxycarbonyl, or benzyloxycarbonyl, $R_2$ is an alkyl of 1 to 3 carbon atoms, and $\Delta$Phe is dehydrophenylalanine. For Formulas II–V, $R_1$ is H or a protecting group at the amino terminus of the type tert butyloxycarbonyl(-BOC), 9-fluorenylmethyloxycarbonyl, or benzyloxycarbonyl, $R_2$ is an alkyl of 1 to 3 carbon atoms, $R_5$ is hydrogen or an alkyl of 1 to 3 carbon atoms, and $\Delta$Phe is dehydrophenylalanine.

DESCRIPTION OF THE PREFERRED EMBODIMENTS

This invention describes novel oligopeptide compounds which possess phytotoxic and plant growth regulating properties as observed in detached wheat coleoptile or lettuce and curly cress seedling assays. These bioassays are used to screen potential oligopeptide herbicides and plant growth regulators. It comprises a novel and facile synthetic route for the preparation of a series of linear amino and carboxylate protected tri- and tetra-peptides which demonstrate root growth promotion or root growth inhibition. The novel linear oligopeptides of this invention include:

I. $R_1$-N($R_2$)-D,L-Ala-D,L-Leu-N($R_2$) $\Delta^z$Phe-Gly-O$R_3$;
II. $R_1$-D,L-Leu-N($R_2$) $\Delta^z$Phe-Gly-O$R_3$;
III. $R_1$-Aib-N($R_2$) $\Delta^z$Phe-Gly-O$R_3$;
IV. $R_1$-Ala-N($R_5$) $\Delta^z$Phe-Gly-O$R_3$;
V. $R_1$-Val-N($R_2$) $\Delta^z$Phe-Gly-O$R_3$;

for Formula I, $R_1$ is H or a protecting group at the amino terminus of the type 9-fluorenylmethoxycarbonyl, or benzyloxycarbonyl, $R_2$ is an alkyl of 1 to 3 carbon atoms, $R_3$ is hydrogen or an alkyl of 7 to 3 carbon atoms, and $\Delta^z$Phe is dehydrophenylalanine denoting sp$^2$ hybridization at the $\alpha$-carbon of phenylalanine of the z configuration. For Formulas II–V, $R_1$ is H or a protecting group at the amino terminus of the type tert-butyloxycarbonyl(BOC), 9-fluorenylmethyloxycarbonyl, or benzyloxycarbonyl, $R_2$ is an alkyl of 1 to 3 carbon atoms, $R_3$ is hydrogen or an alkyl of 2 to 3 carbon atoms, $R_5$ is hydrogen or an alkyl of 1 to 3 carbon atoms, and $\Delta^z$Phe is dehydrophenylalanine denoting sp$^2$ hybridization at the $\alpha$-carbon of phenylalanine of the z configuration.

Applicants' preferred embodiments of this invention comprises the incorporation of structural peptide backbone changes which increase conformational constraint, and vary the orientation of amino acid side chains when constrasted with naturally occurring amino acid sequences. Additionally, variation in lipophilicity is examined as a paramater in the plant growth regulators that were found to be root growth inhibitors and root growth promoters. Rooth growth inhibition/-promotion was measured in germinating lettuce (*Lactuca sativa*) cv. Northern Lakes and curly cress (*Lepidium sativum*) seedling assays nominally used for screening herbicidal compounds and in a wheat coleoptile assay used for generally screening biological activity. Only compounds exerting measurable biological activities at $1 \times 10^{-6}$M in concentration in the lettuce and cress assays and $1 \times 10^{-3}$M in the wheat coleoptile are claimed. Compounds demonstrating little or no activity were used in assessment of the relative structure-function properties of the analogs.

It should be noted that the prior art has been confined to naturally occurring cyclic tetrapeptides, the phytotoxicity of which has been solely attributed to the most favored conformation adopted by the cyclic tetrapeptide. Thus, the prior art teaches that the molecule must be a cyclic tetrapeptide as a first and directly linked requirement for biological activity to occur. The present invention claims synthetic linear peptides which would have been predicted as biologically inactive based on the prior art. Indeed the present invention claims compounds which demonstrate an altogether different type of biological activity.

Physical constants are reported as follows: Thin layer chromatography (TLC) $R_f$ values were determined on silica gel plates using the developing solvents N-butanol/acetic acid/water, 4:1:1 (v/v) (A), and ethyl acetate/hexane/acetone 2:1:1 (v/v) (B), melting points, M.P.; optical rotations, $[\alpha]_D$; proton nuclear magnetic resonance ($H^1NMR$), and fast atom bombardment mass spectroscopy, FAB MS.

SYNTHESIS

P-toluenesulfonate D,L-3-phenylserine ethyl ester (Compound 1)

An ethanol solution (50 ml) of p-toluenesulfonic acid (0.067 moles, 12.7 g) and D,L-3 phenylserine (0.033 mol, 6.0 g) was refluxed for 24 h. The solvent was removed and the resulting residue repeatedly washed (approximately 4 times) with ether using vacuum filtration, yielding a white solid (12.8 g) (yield, 95%): $R_f(A)$ 0.63, m.p. 161–163, $H^1NMR$ ($CDCl_3$) δ: 0.97 (t, 3H, O—$CH_2$—$CH_3$), 2.33(S, 3H, $H_3C$-Ar), 3.19 (t, 1H, CH-Ar), 3.90(d, 1H, OH, exchanged $D_2O$), 3.98(q, 2H, O'$CH_2$), 4.05(d, 1H, CH-Ar) 7.5(q, 4H, (tosyl)).

Boc-Leu-D,L-Phe(β-OH)-OH (Compound 2)

A solution of 1.7 g (0.0075 mol) of Boc-Leucine in 30 ml of dry tetrahydrofuran was cooled to −5° C. and 0.99 g (0.0089 mol) of N-methylmorpholine and 1.0 g (0.0075 mol) of isobutyl chloroformate were added and stirred for 1 h. A solution of compound 1 (3.0 g, 0.0075 mol) in 10 ml of dioxane:water (7:3) (v/v) containing (0.0089 mol) 0.909 g of triethylamine was added. The mixture was stirred for 3 at ambient temperature, approximately 20 ml water was added and the tetrahydrofuran was evaporated in vacuo. The resulting oil was extracted with ethyl acetate (80 ml) and the pooled extracts were washed sequentially with 1N-hydrochloric acid, sat'd sodium bicarbonate solution, sat'd sodium chloride solution and dried over anhydrous $Na_2SO_4$. The solvent was removed in vacuo yielding an oil: 2.9 g (0.007 mol, yield 94%); homogeneous on TLC $R_f(A)$ 0.91, $R_f(B)$ 0.70). The resulting ester was dissolved in 20 ml of methanol and 20 ml of 1N sodium hydroxide was added. The mixture was stirred for 3 h at ambient temperatures and then concentrated in vacuo. The aqueous solution was acidified with 4N-hydrochloric acid while stirring on ice and then extracted with ethyl acetate. The pooled extracts were washed with sat'd sodium chloride, dried over sodium sulfate and evaporated in vacuo to yield a clear oil: (2.7 g, 95% yield; $R_f(A)$ 0.79, $R_f(B)$ 0.83; $[\alpha]_D^{25}$ −22.2° (c 1, MeOH); $H^1NMR$ ($CDCl_3$) δ: 0.95 (m, 7H, $H_3C$—CH—$CH_3$), 1.17(m, 2H, $CH_2$) 1.4 (s, 9H, Boc), 2.15(m, 1H, NH—CH—C(O)) 4.05(d, 1H, CH—COH), 4.15(d, 1H, CH—COOH), 4.6 (s, 1H, OH, exchanged by $D_2O$), 4.75(d, 1H, C(O)—NH, exchanged by $D_2O$) 4.8(d, 1H, C(O)—NH, exchanged $D_2O$, 7.3(s, 5H, ArH), 9.5(b, 1H, COOH) Anal. Calcd for $C_{20}H_{30}O_6N_2$: C 60.91, H, 7.61N, 7.10., Found: C, 60.89H, 7.62, N, 7.08.

Azlactone of Boc-Leu-Δ$^z$Phe (Compound 3)

A solution of 2.3 g (0.006 mol) of compound 2 and 0.4 g of sodium acetate in 6 ml of acetic anhydride was stirred at room temperature for 8 h. The reaction was evaporated in vacuo to dryness. The resulting residue was stirred with ethyl acetate (60 ml) and water (20 ml) and the water layer separated from the ethyl acetate. The ethyl acetate extract was washed with sat'd sodium bicarbonate solution, and dried over anhydrous sodium sulfate. The solvent was evaporated in vacuo and the resulting white solid was recrystallized from ether/hexane yielding: 1.86 g, 0.0054 moles (90% yield); m.p. 118°–120° C.; $[\alpha]^{25}$ 107.38° (c. 1, MeOH); H'NMR($CDCl_3$) δ: 0.95(m, 7H, $H_3C$—CH—$CH_3$), 1.17(m, 2H, $CH_2$), 1.4 (s, 9H, Boc), 2.1 (m, 1H, CH—$CH_2$), 4.9 (bs, 1H, NH—C(O), 7.25-7.7 (m, 6H, PhCH=C); Anal. Calcd for $C_{20}H_{28}O_3N_2$: C, 69.77, H, 8.14N, 8.19: Found C, 69.70, H 8.06, N, 8.09.

Boc-Leu-Δ$^z$Phe-Gly-OMe (Compound 4)

Glycine methyl ester hydrochloride 0.063 g (0.791 g) was equilibrated in a stirred mixture of 20 ml aqueous 50% potassium carbonate and 50 ml ethyl acetate on a cooled ice bath. The ethyl acetate layer was separated and dried over anhydrous $Na_2SO_4$ at 0° C. To this solution compound 3 (0.053 mol, 1.99 g) was added and refluxed for 8 h. The solution was cooled and washed sequentially with 1N HCl, sat'd sodium bicarbonate solution, sat'd sodium chloride solution, and dried over anhydrous $Na_2SO_4$. The solvent was removed and the resulting white solid was recrystallized from ethyl acetate/hexane yielding: 0.004 mol (2.0 g, 84% yield) of 4; m.p. 135°–138° C.; $R_f(A)$ 0.87, $R_f(B)$ 0.68; $[\alpha]^{25}$ −42.95° (c 1, MeOH); $H^1NMR$ ($CDCl_3$) δ:0.95(m, 7H, $H_3C$—CH—$CH_3$), 1.2(m, 2H, $CH_2$), 1.4 (s, 9H, Boc), 2.1(m, 1H, CH), 3.9(s, 3H, O—$CH_3$), 4.15(d, 2H, HN—$CH_2C$(O)), 5.1-5.3 (bm, 3H, amide H's, exchanged with $D_2O$), 7.35-7.7 (m, 6H, PhCH=C), Anal Calcd for $C_{22}H_{33}O_6N_3$; C, 60.69, H, 7.59, N 9.65: Found C, 60.62, H, 7.53, N, 9.58.

Boc-N($CH_3$)Ala-Leu-N($CH_3$)Δ$^z$Phe-Gly-OMe (Compound 5) and Procedure for Similar Tetrapeptides Compound 4 (0.0044 moles, 1.89 g) was dissolved in a 40% trifluoroacetic acid in methylene chloride solution. The solution was stirred for 30 min at room temperature and the trifluoroacetic acid and methylene chloride were removed in vacuo and dried over $P_2O_5$. The trifluoroacetate salt was dissolved in 20 ml of dry degassed DMF and the solution was cooled to 0° C. on an ice bath. The solution pH was adjusted to approximately 7.0 with N-methylmorpholine (NMM). Boc-N($CH_3$) Alanine (0.004 moles, 0.89 g) was added, followed by dicyclohexylcarbodiimide (0.004 mol, 0.91 g) and hydroxybenzotriazole (0.004 mole, 0.59 g). The reaction was allowed to proceed for approximately 12 h. The solvent was evaporated and the resulting residue was mixed with ethyl acetate. Undissolved dicyclohexylurea (DCU) was filtered; the filtrate was allowed to stand at 0° C. for 3 h and the residual DCU was filtered. The solution was washed sequentially with 1N hydrochloric acid, sat'd sodium bicarbonate, sat'd sodium chloride, and the solution dried over anhydrous $Na_2SO_4$. The solvent was evaporated yielding 2.1 g (0.0039 mol, 88% yield) of a light yellow oil, $R_f(A)$ 0.86, $R_f(B)$ 0.88. The protected linear tetrapeptide ester (0.52 g, 0.001 mol) was subject to selective N-methylation at dehydrophenylalanine as outlined by Rich, D. H., Tam, J. Mathiaparanum, P., [Synthesis, p. 402, (1975)], the procedures of which are herein incorporated by reference. The reaction was evaporated of solvent and the resulting residue mixed with ethyl acetate. The ethyl acetate mixture was washed sequentially with water, 1N hydrochloric acid, sat'd sodium bicarbonate, sat'd sodium chloride, and dried over anhydrous $Na_2SO_4$. The solvent was removed resulting in 0.44 g (0.8 mmol, 80% yield) of compound 5. $[\alpha]^{25}$8.00° (c 1.1, MeOH); $H^1NMR$ ($CDCl_3$) δ:0.5-0.6, (m, 7H, $CH_3$—CH—$CH_3$), 1.3 [(m, 3H, CH$_3$(Hs of Ala)], 1.4 (s, 9H, Boc), 2.7 [s, 3H, N—CH$_3$ (Ala)] 3.7 (s, 3H, O—CH$_3$), 4.1 (d, 2H, CH$_2$'CO); 4.6[m, αH, Gly]. 5.1–5.3 (bs, 1H, NH(exchanged D$_2$O)), 6.5 (bs, 1H, NH(exchanged D$_2$O)), 7.35–7.7 (M, 6H, PhCH=C), (FAB MS calcd MH+453 found MH+453).

The following examples set forth the preferred embodiments of the invention:

EXAMPLE 1

Formula I:
R$_1$-N(R$_2$)-D,L-Ala-D,L-Leu-N(R$_2$)ΔPhe-Gly O-R$_3$

In general, compounds of the general structure shown by Formula I are produced by synthesis of compound 5. Detailed instructions are described supra in the specification for synthesizing compounds 1 through 5.

Boc-N(CH$_3$)-Ala-Leu-N(CH$_3$)Δ$^z$Phe-Gly-OMe (Table I, compound 5); was synthesized through completion of synthetic procedures outlined for compounds 1 through 5 supra, and was tested in germinating plant seedling assays with lettuce and cress seeds which are nominal herbicidal assays. Positive phytotoxic results are shown in Table I and II.

IN GENERAL FOR EXAMPLES 2–5

Tripeptides of the type illustrated in Examples 2–5 infra differ only in the amino acid and sterochemistry at position 1. They are produced using the outlined synthesis of the specification starting with compound 1 and proceeding through compound 4. In order to accomplish N-alkylation at the dehydrophenylalanine position, compounds in Formulas II–V can be selectively alkylated with methyl iodide or ethyl iodide through combination of the protected tripeptide ester with an 8 equivalent excess of potassium carbonate, a 10 equivalent excess of alkyl iodide, and 0.5 equivalents of 18-crown-6 in dimethylformamide. The reaction is stirred vigorously for 72 h, diluted with ethyl acetate and filtered. The filtrate is washed sequentially with water, in citric acid solution, water, sodium hydrogencarbonate, water, dried (Na$_2$SO$_4$) and evaporated in vacuo to give the N-methylated product.

Compounds of Formulas II–V are tripeptides of the type illustrated in Formulas II–V and differ only in the amino acid and sterochemistry at position 1. R groups are derivable as follows: R$_1$ is derived through classic peptide synthetic methods for protecting amino acids. R$_2$ is derived through utilizing selected alkyl iodides of 1 to 3 carbon atoms; R$_3$ is derived through classic esterification methods of amino acids to form ethyl or methyl esters.

EXAMPLE 2

Formula II: R$_1$-D,L-Leu-N(R$_2$)ΔPhe-Gly-OR$_3$

Compounds of the general structure shown by Formula II are produced by synthesis of compound 4 followed by selective N-alkylation by the method outlined in Rich et al. (Rich, D. H., Tam, J. Mathiaparanum, P., Synthesis. 402, 1975), the procedures of which are herein incorporated by reference. Other detailed instructions are described supra in the specification for synthesizing compound 4. To synthesize compounds of Formula II use D or L-leucine at the one position.

Boc-Leu-N(C$_2$H$_5$)Δ$^z$Phe-Gly-OMe (Table I, Compound 6) was synthesized through completion of synthetic procedures outlined for compounds 1 through 4 supra, which was followed by selective N-alkylation with ethyl iodide as outlined supra for procedures for compound 5, and tested in germinating plant seedling assays with lettuce and cress seeds as well as in a detached coleoptile assay with wheat, all of which are nominal herbicidal assays. The results as reported in Tables I and II show plant growth stimulation and phytotoxicity.

EXAMPLE 3

Boc-D-Leu-N(C$_2$H$_5$)Δ$^z$Phe-Gly-OMe (Table I, Compound 7) was synthesized the same as Example 2 except Boc-D-Leu was employed. Compound 7 was then tested the same as in Example 2 and the results shown on Tables I and II indicate plant growth inhibition and phytotoxicity.

EXAMPLE 4

Boc-Leu-N(CH$_3$)Δ$^z$Phe-Gly-OMe (Table I, Compound 8) was synthesized the same as Example 2 except methyl iodide was used instead of ethyl iodide for the N-alkylation. Compound 8 was tested the same as in Example 2 and results as shown in Tables I and II indicate plant growth inhibition and phytotoxicity.

FMOC-Leu-N(CH$_3$)Δ$^z$-Phe-Gly-Ome (Table II, Compound 15), was synthesized the same as compound 8, except FMOC was substituted for BOC. Compound 15 was tested in Wheat Coleoptile assay and the results are reported in Table II and indicated plant growth inhibition.

EXAMPLE 5

Formula III:R$_1$-Aib-N(R$_2$)ΔPhe-Gly-OR$_3$

Compounds of the general structure shown in Formula III are produced as described in Example 2; however, in synthesizing compounds of Formula III use amino isobutyric acid (Aib) at the 1 position.

Boc-Aib-N(CH$_3$)Δ$^z$Phe-Gly-OMe (Table I, Compound 9) was synthesized the same as Example 4 except Boc-Aib was utilized in place of Boc-Leu. Compound 9 was then tested the same as in Example 4 and plant growth stimulation and phytotoxic results were reported in Tables I and II.

Boc-Aib-Δ$^z$Phe-Gly-OMe, (Table I, Compound 14) was synthesized the same as compound 9 except Boc-Aib is substituted for Boc-Leu. Compound 14 was tested the same as compound 9 and the results which indicated no activity as an inhibitor or a promoter are shown on Table I.

EXAMPLE 6

Formula IV: R$_1$-D,Ala-N(R$_2$)ΔPhe-Gly-OR$_3$

Compounds of the general structure as shown in Formula IV are produced as described in Example 2 except in synthesizing compounds of Formula IV use D-alanine at the one position.

Boc-D-Ala-Δ$^z$Phe-Gly-OMe (Table I, Compound 10) was synthesized following procedures from Compounds 1 through 3 supra, except Boc-D-Ala was used instead of Boc-Leu. Compound 10 was then tested as in Example 2 and root growth inhibition and phytotoxic results were reported in Tables I and II.

EXAMPLE 7

Formula V: R$_1$-Val-N(R$_2$)ΔPhe-Gly-OR$_3$

Compounds of the general structure as shown in Formula V are produced as described in Example 2;

however, in synthesizing compounds of Formula V use valine at the one position.

Boc-Val-N(C$_2$H$_5$)$\Delta^z$Phe-Gly-OMe (Table I, Compound 11) was synthesized using the same procedures of Example 2 except Boc-Valine was used in place of Boc-Leu. Compound 11 was tested and plant growth promotion and phytotoxicity results were reported in Tables I and II.

Boc-Val-N(CH$_3$)$\Delta^z$Phe-Gly-OMe (Table I, Compound 12) was synthesized using the same procedures of Example 3 except Boc-Val is substituted for Boc-Leu. Compound 12 was tested the same as in Example 3 and plant growth inhibition and phytotoxic properties were recorded in Tables I and II.

BIOASSAY

Root Growth Bioassay of Germinating Lettuce and Curly Cress Seedlings

ROOT GROWTH REGULATING ACTIVITY IN LETTUCE AND CRESS SEEDLINGS

Linear tetrapeptides, tripeptides, their N and C terminal protected analogs, of the general Formulas I–V and the constituent amino acids were produced by the denoted synthesis supra and assayed for root growth regulating activity in lettuce and cress seedlings. A minimal sequence of three amino acids (tripeptide) yielded optimal activity in both stimulating and inhibiting root growth. Peptide analogs which were deprotected at either the amino or carboxylate termini in most instances demonstrated less activity than the completely protected analog. Peptide analogs N-alkylated at dehydrophenylalanine were active at $1 \times 10^{-6}$M. Listed in Table I are those peptide analogs which demonstrated either a growth inhibiting or stimulating effect on germinating lettuce and cress seedlings.

TABLE I

| | % Root Growth | | |
|---|---|---|---|
| | *Promotion | *Inhibitor | Phytotoxicity |
| 5  Boc—N(CH$_3$)—Ala—Leu—N(CH$_3$)$\Delta^z$Phe—Gly—OMe | | | + |
| 6  Boc—Leu—N(C$_2$H$_5$)$\Delta^z$Phe—Gly—OMe | 40–50% (L), 10% (C) | | + |
| 7  Boc—D-Leu—N(C$_2$H$_5$)$\Delta^z$Phe—Gyl—OMe | | 50% (L), 80% (C) | + |
| 8  Boc—Leu—N(CH$_3$)$\Delta^z$Phe—Gly—OMe | | 60% (L), 50% (C) | + |
| 9  Boc—Aib—N(CH$_3$)$\Delta^z$Phe—Gly—OMe | 40% (L), 90% (C) | | + |
| 10  Boc—D-Ala—$\Delta^z$Phe—Gly—OMe | | 40% (L), 20% (C) | + |
| 11  Boc—Val—N(C$_2$H$_5$)$\Delta^z$Phe—Gly—OMe | 40% (C) | | + |
| 12  Boc—Val—N(CH$_3$)$\Delta^z$Phe—Gly—OMe | | 85% (C) | + |
| 13  Cyclo[—N(CH$_3$)Ala—Leu—N(CH$_3$)—$\Delta^z$Phe—Gly—]** | *(Not active as a inhibitor) (or promoter) | | +based on chorosis induction |
| 14  Boc—Aib—$\Delta^z$Phe—Gly—OMe | (Not active as a inhibitor) (or promoter) | | |

*Percent root growth promotion or inhibition at $10^{-6}$ M.
**Tentoxin was obtained from Sigma Chemical Co., P. O. Box 14508, St. Louis, MO 63178, as an isolate from fermentation cultures.
L denotes lettuce seedling assay and C denotes curley cress seedling assay.

Aliquots of tested oligopeptide compounds of the type Formulas I–V were dissolved in ethyl acetate. One milliliter aliquots of the samples were pipetted onto a 4.25 mm filter disk, dried, and placed in a Petri dish. One mL of distilled water was pipetted onto the filter paper and 15 lettuce seeds were uniformly distributed on the surface of the filter paper and allowed to imbibe in the dark at 20° to 25° C. for 24 h. The samples were subsequently placed in a growth chamber under continuous light at 28° C. for 72 h, and the root lengths were measured.

During the course of these assays, visual assessment of seedling vigor was made in addition to root length measurements. Plants exposed to the claimed compounds were designated as phytotoxic if they exhibited either chlorosis and/or necrosis of tissues when compared with untreated control plants. Assessment of phytotoxicity was not confined to assessment of the root, but included any organ of the assay species.

WHEAT COLEOPTILE ASSAY

An assay previously utilized for detecting growth inhibition and promotion and cited for its validity in screening for phtotoxicity was employed. The techniques utilized were those of Cutler et al. (Cutler, H. G., Crumley, F. G.; Cox, R. H.; Davis, E. E.; Harper, L.; Cole, R. J.; Sumner, D. S. *J. Argic. Food Chem.* 1982, 30 658); the procedures of which are herein incorporated by reference.

DISCUSSION OF BIOASSAY RESULTS

The results for a structure-function study in the lettuce and cress seedling assays and the wheat coleoptile assay are reported for modified tripeptide analogs of the type shown in the following structure:

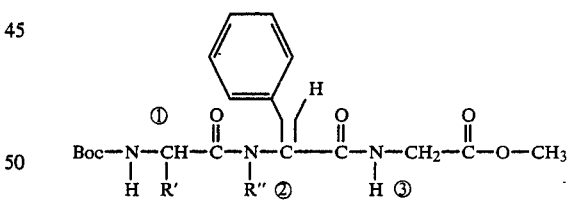

The general structure of the tripeptide analogs contain a N-terminal Boc protecting group and numbered amino acid positions are indicated in circles. R' and R" vary depending on the analog. The protected tetrapeptide 5 demonstrated phytotoxic properties in the form of root growth inhibition leading to early mortality in the cress and lettuce seedling. A visual assessment of the growth of lettuce and cress seedlings treated with this analog yielded initially critical observations on the root growth inhibiting properties manifested in the early stages of this study. Furthermore, the discovery of this compound possessing root growth inhibiting properties led to the development of the novel phytotoxic peptides claimed. In this regard it is important to note (Table 1) that although tentoxin (commercial compound 13) induces chlorosis in lettuce seedlings which can be construed as phytotoxic, it manifested none of the plant growth inhibiting or promoting properties observed with the peptides of this specification.

The results shown in Table I indicate that both variation in stereochemistry at position 1 (aminoacid positions are numbered from the amino terminus: see above structure) and N-alkylation at dehydrophenylalanine (position 2) affect root growth promotion and inhibition. A change of L-leucine in compound 6 to D-leucine in compound 7 gives a shift in measurable plant growth regulation from promotion to inhibition. Incorporation of aminoisobutyric acid (Aib) at position 1 when combined with N-methylation at dehydrophenylalanine gives root growth promotion as observed with compound 9. However, a similar compound (compound 14, Table I) without N-methylation at dehydrophenylalanine showed no effect at $10^{-6}$M concentration. Based on results of 7, 8 and 9, both N-alkylation at the 2 position and a D-amino acid at the 1 position give root growth inhibition, but, a combination of the two exert a stronger inhibitory effect.

It is interesting that Aib introduces increased steric constraint upon substituting it for a naturally occurring amino acid in a peptide. This effect when combined with N-methylation at the 1 position may have caused the shift from inhibition seen in 8 to promotion in 9. Structure-function studies thus demonstrate that the orientation of the alkyl side chain of the amino acid at the 1 position with respect to N-alkylation at the 2 position alters root growth in germinating lettuce seedlings. It is hypothesized that N-alkylation at the 2-position is restricting the torsional angle in the peptide backbone, which when coupled with the sp$^2$ center of the dehydroamino acid fixes the $\chi$, angle and/or the 1-position aliphatic amino acid (D or L) gives a critical orientation of side chains that produce the observed effect. It is noteworthy that lipophilicity versus charge was assessed at the N and C termini of analogs of Formula I by testing amino and carboxylate deprotected analogs. Thus, compound 5, Boc-N(CH$_3$)Ala-Leu N(CH$_3$)$\Delta^z$Phe-Gly-OMe, was active at $10^{-6}$M but when the N and C terminal protecting groups were removed a decrease in activity was observed. Compounds protected at the amino but not carboxylate terminus and vice versa were more active than the completely deprotected analog.

The results of the wheat coleoptile assay are shown in Table 2 infra. Based on these results it is apparent that all compounds with the exception of 10 demonstrated either growth inhibition, promotion or both. An interesting structure-function relation which emerges from this data is found in compounds 6 and 11 which demonstrated growth inhibition at $10^{-3}$M and slight promotion at $10^{-4}$M. Compounds 6 and 7 differ from other compounds only in their N-alkylation at dehydrophenylalanine and the presence of an L-amino acid. The compounds 6 and 7 are similar by virtue of N-alkylation with an R$_2$ ethyl functionality. Compound 10 showed no activity in this assay and is the only analog with the absence of N-alkylation at the 3-position. Of the analogs treated in this assay the most potent were 9 and 15 which also are the most conformationally rigid and lipophilic, respectively. Since the synthesized peptides exhibit phytotoxic and plant growth regulating effects, the compounds have potential value as herbicides and/or plant growth regulators. Due to their peptide backbone constraint conferred by N-alkylated and dehydroamino acids they are ideally suited for conformational (NMR and CD) and computational chemistry (computer graphics) analysis for determining critical bond angle and side chain distances in giving maximal herbicidal activity.

TABLE II

WHEAT COLEOPTILE ASSAY OF CLAIMED COMPOUNDS

| | Growth Regulating | |
|---|---|---|
| | Promotion* | Inhibition* |
| 6 Boc—Leu—N(C$_2$H$_5$)$\Delta^z$Phe—Gly—OMe | 17.8($10^{-4}$) | 13.25($10^{-3}$) |
| 7 Boc—D-Leu—N(C$_2$H$_5$)$\Delta^z$Phe—Gly—OMe | | 14.9($10^{-3}$) |
| 8 Boc—Leu—N(CH$_3$)$\Delta^z$Phe—Gly—OMe | | 14($10^{-3}$) |
| 9 Boc—Aib—N(CH$_3$)$\Delta^z$Phe—Gly—OMe | | 14($10^{-3}$) |
| 10 Boc—D-Ala—$\Delta^z$Phe—Gly—OMe | (NOT ACTIVE) | |
| 11 Boc—Val—N(C$_2$H$_5$)$\Delta^z$Phe—Gly—OMe | 17.7($10^{-4}$) | 13.2($10^{-3}$) |
| 12 Boc—Val—N(CH$_3$)$\Delta^z$Phe—Gly—OMe | | 12($10^{-3}$) |
| 15 FMOC—Leu—N(CH$_3$)$\Delta^z$Phe—Gly—Ome | | 12.0($10^{-3}$) |
| Control | 17.1 | |

*Statistically significant coleoptile lengths are listed in millimeter × 3. The concentration of the active compound is indicated in parenthesis.

We claim:

1. A method of producing phytotoxic and plant growth regulating properties in a plant comprising applying an effective amount of the phytotoxic and plant growth regulating compound R$_1$-N(R$_2$)-D,L-Ala-D,L-Leu-N(R$_2$)$\Delta^z$Phe-Gly-OR$_3$;

in which R1 is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms, and $\Delta^z$Phe is dehydrophenylalanine denoting sp$^2$ hybridization at the $\alpha$-carbon of phenylalanine of the z configuration, to the locus of said plant before, during or after the seeding of said plant.

2. The method of claim 1 wherein the compound is Boc-N(CH$_3$)Ala-Leu-N(CH$_3$)$\Delta^z$Phe-Gly-OMe.

3. The compound Boc-Leu-N(C$_2$H$_5$)$\Delta^z$Phe-Gly-OMe, wherein Boc is tert-butyloxycarbonyl.

4. A method of producing phytotoxic and plant growth regulating properties in a plant comprising applying an effective amount of the phytotoxic and plant growth regulating compound R$_1$-D,L-Leu-N(R$_2$)$\Delta^z$Phe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms and $\Delta^z$Phe is dehydrophenylalanine denoting sp$^2$ hybridization at the α-carbon of phenylalanine of the z configuration, to the locus of said plant before, during or after the seeding of said plant.

5. The method of claim 4 wherein the compound Boc-Leu-N(C$_2$H$_5$)Δ$^z$Phe-Gly-OMe is applied to the locus of the plant.

6. The method of claim 4 wherein the compound Boc-Leu-N(CH$_3$)Δ$^z$Phe-Gly-OMe is applied to the locus of the plant.

7. An oligopeptide compound which possesses plant growth regulating properties comprising the general formula R$_1$-Aib-N(R$_2$)ΔPhe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms and ΔPhe is dehydrophenylalanine.

8. The compound of claim 7 wherein ΔPhe is Δ$^z$Phe and denotes dehydrophenylalanine of the z configuration with sp$^2$ hybridization at the α-carbon of phenylalanine.

9. The compound of claim 7 wherein the compound is Boc-Aib-N(CH$_3$)Δ$^z$Phe-Gly-OMe.

10. A method of producing plant growth regulating properties in a plant comprising applying an effective amount of plant growth regulating compound R$_1$-Aib-N(R$_2$)Δ$^z$Phe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms and Δ$^z$Phe is dehydrophenylalanine denoting sp$^2$ hybridization at the α-carbon of phenylalanine of the z configuration of the locus of said plant, before, during or after the seeding of said plant.

11. The method of claim 10 wherein the compound Boc-Aib-N(CH$_3$)Δ$^z$Phe-Gly-OMe that is applied to the locus of the plant.

12. An oligopeptide compound which possesses phytotoxicity and plant growth regulating properties comprising the general formula R$_1$-D,L-Ala-NR$_5$ΔPhe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_5$ is hydrogen or an alkyl of 1 to 3 carbon atoms, R$_3$ is hydrogen or an alkyl of 1 to 3 carbon atoms and Δ Phe is dehydrophenylalanine.

13. The compound of claim 12 wherein ΔPhe is Δ$^z$Phe and denotes dehydrophenylalanine of the z configuration with sp$^2$ hybridization at the α-carbon of phenylalanine.

14. The compound of claim 12 wherein the compound is Boc-D-Ala-Δ$^z$Phe-Gly-OMe.

15. A method of producing phytotoxic and plant growth regulating properties in a plant comprising applying an effective amount of the phytotoxic and plant growth regulating compound R$_1$-D,L-Ala-NR$_5$Δ$^z$Phe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_5$ is hydrogen or an alkyl of 1 to 3 carbon atoms, R$_3$ is hydrogen or an alkyl of 1 to 3 carbon atoms, and Δ$^z$Phe is dehydrophenylalanine denoting sp$^2$ hybridization at the α-carbon of phenylalanine of the z configuration, to the locus of said plant, before, during or after the seeding of said plant.

16. The method of claim 15 wherein the compound Boc-D-Ala-Δ$^z$-Phe-Gly-OMe is applied to the locus of the plant.

17. An oligopeptide compound which possesses phytotoxicity and plant growth regulating properties comprising the general formula R$_1$-Val-N(R$_2$) ΔPhe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms and Δ Phe is dehydrophenylalanine.

18. The compound of claim 17 wherein ΔPhe is Δ$^1$Phe and denotes dehydrophenylalanine of the z configuration with sp$^2$ hybridization at the α-carbon of phenylalanine.

19. The compound of claim 17 wherein the formula is Boc-Val-N(C$_2$H$_5$)Δ$^z$Phe-Gly-OMe.

20. The compound of claim 17 wherein the formula is Boc-Val-N(CH$_3$)Δ$^z$Phe-Gly-OMe.

21. A method of producing phytotoxic and plant growth regulating properties in a plant comprising applying an effective amount of the phytotoxic and plant growth regulating compound R$_1$-Val-N(R$_2$)Δ$^z$Phe-Gly-OR$_3$;

in which R$_1$ is H or a protecting group at the amino terminus of the type tert-butyloxycarbonyl (BOC), 9-fluorenylmethyloxycarbonyl, or benzyloxycarbonyl, R$_2$ is an alkyl of 1 to 3 carbon atoms, R$_3$ is hydrogen or an alkyl of 1 to 3 carbon atoms and Δ$^z$Phe is dehydrophenylalanine denoting sp$^2$ hybridization at the α-carbon of phenylalanine of the z configuration, to the locus of said plant, before, during or after the seeding of said plant.

22. The method of claim 21 wherein the compound Boc-Val-N(C$_2$H$_5$)Δ$^z$Phe-Gly-OMe is applied to the locus of the plant.

23. The method of claim 21 wherein the compound Boc-Val-N(CH$_3$)Δ$^z$Phe-Gly-OMe is applied to the locus of the plant.

* * * * *